US011452476B2

(12) United States Patent
Zang et al.

(10) Patent No.: US 11,452,476 B2
(45) Date of Patent: Sep. 27, 2022

(54) DETECTION REPORT DATA GENERATION METHOD

(71) Applicant: Shanghai Lepu CloudMed Co., Ltd, Shanghai (CN)

(72) Inventors: Kaifeng Zang, Beijing (CN); Haitao Lu, Beijing (CN); Pengfei Zhao, Beijing (CN); Yan Jiang, Beijing (CN); Baoquan Wang, Beijing (CN); Jun Cao, Beijing (CN)

(73) Assignee: Shanghai Lepu CloudMed Co., Ltd, Shanghai (CN)

( * ) Notice: Subject to any disclaimer, the term of this patent is extended or adjusted under 35 U.S.C. 154(b) by 70 days.

(21) Appl. No.: 16/755,113

(22) PCT Filed: Jan. 12, 2018

(86) PCT No.: PCT/CN2018/072358
§ 371 (c)(1),
(2) Date: Apr. 9, 2020

(87) PCT Pub. No.: WO2019/100564
PCT Pub. Date: May 31, 2019

(65) Prior Publication Data
US 2020/0253494 A1 Aug. 13, 2020

(30) Foreign Application Priority Data
Nov. 27, 2017 (CN) .......................... 201711202991.1

(51) Int. Cl.
A61B 5/00 (2006.01)
A61B 5/316 (2021.01)
(Continued)

(52) U.S. Cl.
CPC ............ *A61B 5/316* (2021.01); *A61B 5/0245* (2013.01); *A61B 5/02405* (2013.01); *G16H 15/00* (2018.01); *G16H 50/20* (2018.01)

(58) Field of Classification Search
CPC ... A61B 5/316; A61B 5/02405; A61B 5/0245; A61B 5/7282; A61B 5/372;
(Continued)

(56) References Cited

U.S. PATENT DOCUMENTS

2014/0194762 A1    7/2014  Kuppuraj et al.
2014/0364756 A1*  12/2014  Brockway ............ G06K 9/0053
                                                              600/513
(Continued)

FOREIGN PATENT DOCUMENTS

CN     1393204 A    1/2003
CN   102138789 B    5/2014
(Continued)

OTHER PUBLICATIONS

Chinese 1st Office Action for Chinese Application No. 201711202991.1 dated May 5, 2020, 5 pages.
(Continued)

*Primary Examiner* — Rex R Holmes
*Assistant Examiner* — Sana Sahand
(74) *Attorney, Agent, or Firm* — TraskBritt

(57) ABSTRACT

A detection report data generation method including acquiring event type information of an electrocardiogram event corresponding to electrocardiogram event data, wherein the event data has one or more pieces of event type information; screening the event data according to signal quality evaluation indexes so as to obtain report conclusion data and report entry data; carrying out quality assessment on an event segment included in the event data according to the signal quality evaluation indexes, and determining a pre-
(Continued)

selected sample segment according to a quality assessment result; determining position information of an event heart beat in the pre-selected sample segment, and determining segment interception parameters; carrying out interception processing on the pre-selected sample segment according to the segment interception parameters so as to obtain a typical data segment; generating report graphic data according to the typical data segment; and outputting the entry data, the graphic data and the conclusion data.

9 Claims, 1 Drawing Sheet

(51) Int. Cl.
*G16H 15/00* (2018.01)
*G16H 50/20* (2018.01)
*A61B 5/024* (2006.01)
*A61B 5/0245* (2006.01)

(58) Field of Classification Search
CPC ....... A61B 5/7221; A61B 5/743; A61B 5/318; G16H 15/00; G06K 9/0051
See application file for complete search history.

(56) References Cited

U.S. PATENT DOCUMENTS

| | | |
|---|---|---|
| 2016/0188823 A1 | 6/2016 | Rowlandson et al. |
| 2018/0168471 A1* | 6/2018 | Hanuliak ............... A61B 5/366 |
| 2018/0206752 A1* | 7/2018 | Bardy ..................... A61B 5/35 |

FOREIGN PATENT DOCUMENTS

| | | |
|---|---|---|
| CN | 102697492 B | 8/2014 |
| WO | 99/55228 A1 | 11/1999 |
| WO | 2014/203114 A2 | 12/2014 |
| WO | 2017/182622 A1 | 10/2017 |

OTHER PUBLICATIONS

Chinese 2nd Office Action for Chinese Application No. 201711202991.1 dated Jan. 29, 2021, 8 pages.
European Search Report and Search Opinion Received for EP Application No. 18881963, dated May 31, 2021, 02 pages.
International Search Report for International Application No. PCT/CN2018/072358 dated Aug. 29, 2018, 2 pages.
International Written Opinion for International Application No. PCT/CN2018/072358 dated Aug. 29, 2018, 3 pages.

* cited by examiner

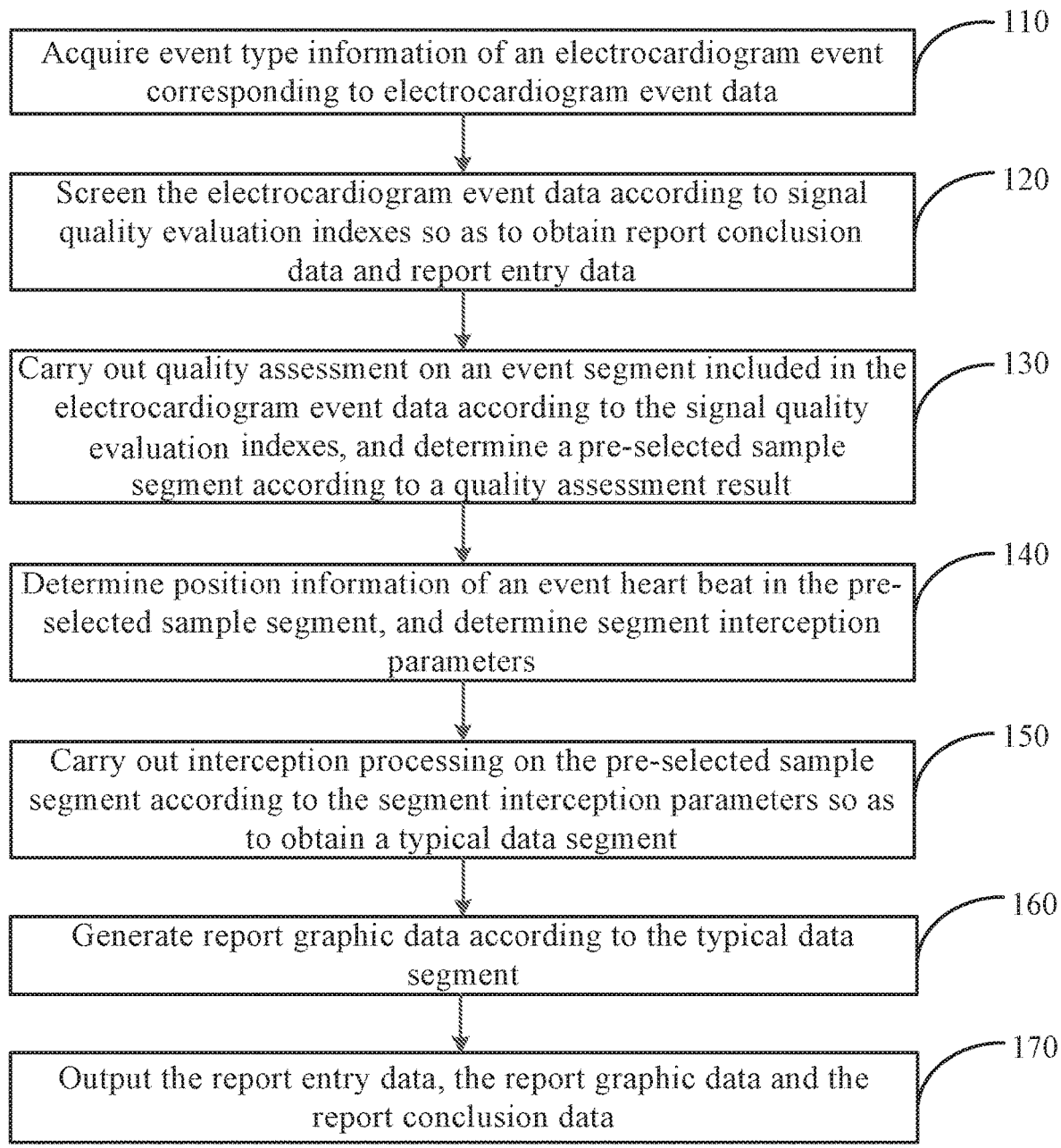

DETECTION REPORT DATA GENERATION METHOD

CROSS-REFERENCE TO RELATED APPLICATIONS

This application is a national phase entry under 35 U.S.C. § 371 of International Patent Application PCT/CN2018/072358, filed Jan. 12, 2018, designating the United States of America and published as International Patent Publication WO 2019/100564 A1 on May 31, 2019, which claims the benefit under Article 8 of the Patent Cooperation Treaty to Chinese Patent Application Serial No. 201711202991.1, filed Nov. 27, 2017.

TECHNICAL FIELD

The present disclosure relates to the technical field of data analyzing and processing, and more particularly, to a method for generating detection report data.

BACKGROUND

Electrocardiogram (ECG) monitoring is an important measure for observation, diagnosis and treatment of cardiovascular patients, and can monitor whether there is arrhythmia, a frequency of heart beat and the like in real time, and thus, timely and effective measures can be taken according to ECG activities. An output of ECG monitoring results is usually realized by generating ECG diagnostic reports.

However, the ECG monitoring, especially ambulatory ECG monitoring, has a very large amount of data. How to obtain required typical data value and the most typical data segments that can most obviously reflect different ECG events for outputting ECG waveforms, from such data is particularly important.

BRIEF SUMMARY

The purpose of the present disclosure is to provide a method for generating detection report date, which can automatically identify a required typical sample segment representing an event type from heart beat analysis data with a signal quality evaluation, and generate detection report data with event type information and the like.

To achieve the above purpose, the present disclosure provides a method for generating detection report date, including:
acquiring event type information of ECG events corresponding to ECG event data, wherein the ECG event data has one or more pieces of event type information;
screening the ECG event data according to signal quality evaluation indexes to obtain report conclusion data and report table item data;
performing a quality evaluation on event segments included in the ECG event data according to the signal quality evaluation indexes, and determining preselected sample segments according to a result of the quality evaluation;
determining position information of an event heart beat in the preselected sample segments, and determining segment interception parameters, wherein the segment interception parameters comprise starting position information and interception width information;
intercepting the preselected sample segments according to the segment interception parameters to obtain a typical data segment;
generating report graphic data according to the typical data segment; and
outputting the report table item data, the report graphic data and the report conclusion data.

Preferably, the intercepting the preselected sample segments according to the segment interception parameters to obtain a typical data segment includes:
intercepting the preselected sample segments according to the starting position information, the interception width information and the position information of the event heart beat, so that a position of the event heart beat is in a middle of the typical data segment obtained by the intercepting.

Preferably, the determining segment interception parameters includes:
determining heart rate data of a first heart beat in the preselected sample segments;
when the heart rate data is greater than an upper limit of a preset threshold, moving forward a first preset displacement parameter according to the position information of the event heart beat to obtain the starting position information;
when the heart rate data is less than a lower limit of the preset threshold, moving forward a second preset displacement parameter according to the position information of the event heart beat to obtain the starting position information.

Further preferably, the determining position information of an event heart beat in the preselected sample segments, and determining segment interception parameters includes:
when the event type information is particular event type information, calculating a proportion of non-interference signals of each data segment in the preselected sample segments according to the quality evaluation index, determining the position information of the event heart beat according to the proportion of the non-interference signals, and determining the interception width information and the starting position information according to segment interception rules corresponding to the particular event type information.

Further preferably, the intercepting the preselected sample segments according to the segment interception parameters to obtain a typical data segment includes:
determining whether the proportion of the non-interference signals reaches a proportion threshold;
performing event type singleness screening on multiple data segments that reach or exceed the proportion threshold; and
determining a data segment with the least heart beat count, in the event type information other than target event type information obtained by the screening, as the typical data segment.

In the method for generating detection report data provided by the embodiments of the present disclosure, the quality evaluation is performed on each type of heart rhythm event by calculating noise interference data, the event segments with the highest data quality are selected, and the number of the event types included in the segments is analyzed. The most representative segment, that is, the segment including only a single heart rhythm event, is preferably selected. The starting position of the segments is preferably selected to ensure the event heart beat is located in the middle of the selected segment. Special rules are preferably set for particular ECG event segments.

BRIEF DESCRIPTION OF THE DRAWINGS

FIG. 1 is a schematic diagram illustrating a method for generating detection report data according to an embodiment of the present disclosure.

DETAILED DESCRIPTION

Technical solutions of the present disclosure will be further described in detail below through accompanying drawings and embodiments.

A method for generating detection report data according to an embodiment of the present disclosure provides a comprehensive and accurate manner for generating ECG detection report data.

FIG. 1 is a schematic diagram illustrating the method for generating detection report data according to an embodiment of the present disclosure. As shown in FIG. 1, the method for generating detection report data of the present disclosure mainly includes the following steps:

Step 110: event type information of ECG events corresponding to ECG event data is acquired.

Specifically, electrical signals are converted into digital signals by an ECG monitoring device for output, which may be single-lead or multi-lead time sequence data. Original data is stored by a data storage and transmission apparatus, and can be transmitted through WIFI, Bluetooth, USB, 3G/4G/5G mobile communication networks, Internet of Things and other means.

Before an ECG signal quality is evaluated, the original data received by transmission needs to be resampled and converted into a preset standard data format by a data format conversion, thereby solving differences in leads, sample frequencies and transmission data formats used by different ECG devices. Converted data in the preset standard data format is processed by digital signal filtering to remove high frequency, low-frequency noise and baseline drift, so as to obtain heart beat data. Interference identification is performed on the heart beat data, and the heart beat data is combined according to results of the interference identification, time rules and lead parameters of the heart beat data to generate heart beat analysis data. The ECG event data is generated from the heart beat analysis data according to heart beat classification information and ECG basic rule reference data.

The ECG event data has corresponding event types, such as supraventricular premature beat, atrial escape beat, ventricular premature beat, ventricular escape beat. The event type information can be set to characterize these event types. Therefore, the ECG event data has one or more event type information.

Step 120: the ECG event data is screened according to signal quality evaluation indexes to obtain report conclusion data and report table item data.

Specifically, the report conclusion data and the report table item data include data obtained by a calculation on heart rate parameters, such as the calculation of an average heart rate, a maximum heart rate and a minimum heart rate. When calculating the maximum and the minimum heart rates, a fixed-length segment is taken as a statistical unit, and whole process scanning and statistical comparison are performed on heart beats one by one. The length of the segment is generally 8-10 seconds, and can be freely set as required. When calculating the heart rate, different statistical calculation methods for heart beat types are adopted for ECG dominated by sinus rhythm and ECG dominated by ectopic rhythm. When calculating the maximum and minimum heart rates, only sinus heart beat is calculated for the ECG dominated by sinus rhythm. For ectopic rhythm ECG dominated by atrial flutter/atrial fibrillation, only atrial flutter/atrial fibrillation heart beat is calculated. For ectopic rhythm ECG dominated by other non atrial flutter/atrial fibrillation ectopic heart beats, all types of heart beats except artifact are involved in the calculation.

Step 130: a quality evaluation is performed on event segments included in the ECG event data according to the signal quality evaluation indexes, and preselected sample segments are determined according to a result of the quality evaluation.

Specifically, according to the signal quality evaluation indexes the quality evaluation is performed for the ECG event data, to select event segments with the highest data signal quality.

Based on the analysis of the heart beat data, the signal quality evaluation indexes is characterized by a noise level within RR intervals with respect to QRS wave complexes. Specifically, the signal quality evaluation indexes may be calculated according to a power of the QRS wave complexes and an average power of noise signals.

Step 140: position information of an event heart beat in the preselected sample segments is determined, and segment interception parameters are determined.

The segment interception parameters are specifically starting position information and interception width information required to confirm a typical data segment, which is also related to a starting position of the event heart beat.

The starting position information and the interception width information may be determined according to types of the ECG events.

When the event type information is general event type information, heart rate data of a first heart beat in the preselected sample segments may be determined first, and then corresponding starting position information can be determined according to the heart rate data of the first heart beat. For example, when the heart rate data is greater than an upper limit of a preset threshold, a first preset displacement parameter is moved forward according to the position information of the event heart beat to obtain the starting position information. when the heart rate data is less than a lower limit of the preset threshold, a second preset displacement parameter is moved forward according to the position information of the event heart beat to obtain the starting position information.

When the event type information is particular event type information, a proportion of non-interference signals of each data segment in the preselected sample segments is calculated according to the quality evaluation index, the position information of the event heart beat is determined according to the proportion of the non-interference signals, and the interception width information and the starting position information are determined according to segment interception rules corresponding to the particular event type information.

It should be understood here that the sample segments may correspond to only one heart beat cycle, or may correspond to multiple heart beat cycles.

Examples are described as below.

It should be noted that there are two manners for processing non-special regular ECG events and special regular ECG events.

First, for the non-special regular ECG events, only a single segment is selected. Since the position of the event heart beat in the preselected sample segments is known, ending position information intercepted in the selected sample segments may be obtained according to the starting position information and the position information of the event heart beat.

For example, when the heart rate of the first heart beat of the segments is greater than or equal to 100, a distance from a starting point of the segments to the first heart beat is 0.3 seconds. When the heart rate of the first heart beat of the segments is less than or equal to 45, the distance from the starting point of the segments to the first heart beat is 0.37 seconds.

Second, for the special regular ECG events, two or more segments may be specified to be intercepted.

The special regular ECG events mentioned in the present disclosure may specifically include three types of events: ventricular tachycardia events, supraventricular tachycardia events, long RR interval events with a time length greater than a preset time threshold; and the preset time threshold is preferably 8 seconds. For these three events, two or more segments can be intercepted. A first segment is extended forward by 3 heart beats, and a second segment is extended backward by 2 heart beats. The starting position of each segment can be processed according to the mentioned-above non-special regular manner.

In addition, when dealing with special regular ECG events, in addition to determining a selected sample segment with a highest proportion as the typical data segment according to the proportion of the non-interference signals, a threshold can also be set. Screening is performed on the sample segments that reach the set threshold, and a sample segment that includes the least number of other event types is selected as the typical data segment. The specific method includes: whether the proportion of the non-interference signals reaches a proportion threshold is determined (preferably, the threshold is determined in a range of 60%-95%); event type singleness screening is performed on data segments that reach or exceed the proportion threshold; and a data segment with the least heart beat count, in the event type information other than target event type information obtained by the screening, is determined as the typical data segment.

The purpose of the singleness screening here is to obtain a sample segment that reflects the event corresponding to the segments as much as possible, that is, try not to have other events.

If there are still multiple sample segments with the least heart beat count obtained through the above steps, a selected sample segment with the highest proportion of the non-interference signals among the multiple selected sample segments is determined as a report sample segment. If the number of the segments is still not unique, a first one of them is selected as a final preference.

Step 150: the preselected sample segments are intercepted according to the segment interception parameters to obtain the typical data segment.

Specifically, the preselected sample segments are intercepted according to the starting position information, the interception width information and the position information of the event heart beat determined in above steps, so that the position of the event heart beat is in a middle of the intercepted selected sample segment, that is, the typical data segment is obtained.

Step 160: report graphic data is generated according to the typical data segment.

Step 170: the report table item data, the report graphic data and the report conclusion data are output.

The report table item data, the report graphic data and the report conclusion data can be output according to a preset data output format.

In the method for generating detection report data provided by the embodiments of the present disclosure, the quality evaluation is performed on each type of heart rhythm event by calculating noise interference data, the event segments with the highest data quality are selected, and the number of the event types included in the segments is analyzed. The most representative segment, that is, the segment including only a single heart rhythm event, is preferably selected. By properly locating the starting position of the segments, it is ensured that the event heart beat is located in the middle of the selected segment, and special rules are preferably set for particular ECG event segments. Finally, combined with the typical data segment and the event type information obtained by the selecting, the detection report data is generated.

Those skilled in the art should further realize that the units and algorithm steps of the examples described in the embodiments disclosed herein can be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc., made within the spirit and principles of the present disclosure should be included in the scope of protection of the present disclosure.

What is claimed is:

1. A method for generating detection report data, comprising:
    acquiring event type information of ECG events corresponding to ECG event data, wherein the ECG event data has one or more pieces of event type information;
    screening the ECG event data according to signal quality evaluation indexes to obtain report conclusion data and report table item data;
    calculating the signal quality evaluation indexes according to a power of QRS wave complexes and an average power of noise signals;
    performing a quality evaluation on event segments included in the ECG event data according to the signal quality evaluation indexes, and determining preselected sample segments according to a result of the quality evaluation;

determining position information of an event heart beat in the preselected sample segments, and determining segment interception parameters, wherein the segment interception parameters comprise starting position information and interception width information;

determining the starting position information and the interception width information according to types of the ECG events;

intercepting the preselected sample segments according to the segment interception parameters to obtain a typical data segment;

generating report graphic data according to the typical data segment; and outputting the report table item data, the report graphic data and the report conclusion data.

2. The method for generating detection report data according to claim 1, wherein the intercepting the preselected sample segments according to the segment interception parameters to obtain the typical data segment comprises:

intercepting the preselected sample segments according to the starting position information, the interception width information and the position information of the event heart beat, so that a position of the event heart beat is in a middle of the typical data segment obtained by the intercepting.

3. The method for generating detection report data according to claim 2, wherein the determining segment interception parameters comprises:

determining heart rate data of a first heart beat in the preselected sample segments;

when the heart rate data is greater than an upper limit of a preset threshold, moving forward a first preset displacement parameter according to the position information of the event heart beat to obtain the starting position information; and when the heart rate data is less than a lower limit of the preset threshold, moving forward a second preset displacement parameter according to the position information of the event heart beat to obtain the starting position information.

4. The method for generating detection report data according to claim 2, wherein the determining position information of an event heart beat in the preselected sample segments, and determining segment interception parameters comprises:

when the event type information is particular event type information, calculating a proportion of non-interference signals of each data segment in the preselected sample segments according to the quality evaluation index, determining the position information of the event heart beat according to the proportion of the non-interference signals, and determining the interception width information and the starting position information according to segment interception rules corresponding to the particular event type information.

5. The method for generating detection report according to claim 4, wherein the intercepting the preselected sample segments according to the segment interception parameters to obtain the typical data segment comprises:

according to the starting position information and the interception width information, intercepting a data segment with the highest proportion of the non-interference signals of each data segment in the preselected sample segments to determine the typical data segment.

6. The method for generating detection report according to claim 4, wherein the intercepting the preselected sample segments according to the segment interception parameters to obtain the typical data segment comprises:

determining whether the proportion of the non-interference signals reaches a proportion threshold;

performing event type singleness screening on multiple data segments that reach or exceed the proportion threshold; and determining a data segment with the least heart beat count, in the event type information other than target event type information obtained by the screening, as the typical data segment.

7. The method for generating detection report data according to claim 3, wherein the determining position information of an event heart beat in the preselected sample segments, and determining segment interception parameters comprises:

when the event type information is particular event type information, calculating a proportion of non-interference signals of each data segment in the preselected sample segments according to the quality evaluation index, determining the position information of the event heart beat according to the proportion of the non-interference signals, and determining the interception width information and the starting position information according to segment interception rules corresponding to the particular event type information.

8. The method for generating detection report according to claim 7, wherein the intercepting the preselected sample segments according to the segment interception parameters to obtain the typical data segment comprises:

according to the starting position information and the interception width information, intercepting a data segment with the highest proportion of the non-interference signals of each data segment in the preselected sample segments to determine the typical data segment.

9. The method for generating detection report according to claim 8, wherein the intercepting the preselected sample segments according to the segment interception parameters to obtain the typical data segment comprises:

determining whether the proportion of the non-interference signals reaches a proportion threshold;

performing event type singleness screening on multiple data segments that reach or exceed the proportion threshold; and determining a data segment with the least heart beat count, in the event type information other than target event type information obtained by the screening, as the typical data segment.

* * * * *